US006763831B2

(12) United States Patent
Sniadach

(10) Patent No.: US 6,763,831 B2
(45) Date of Patent: Jul. 20, 2004

(54) ADJUSTABLE VENTILATION MASK FOR A PATIENT

(76) Inventor: Joseph A. Sniadach, 4427 Wynn Rd., Baltimore, MD (US) 21236

(*) Notice: Subject to any disclaimer, the term of this patent is extended or adjusted under 35 U.S.C. 154(b) by 0 days.

(21) Appl. No.: 09/920,696

(22) Filed: Aug. 2, 2001

(65) Prior Publication Data

US 2003/0024532 A1 Feb. 6, 2003

(51) Int. Cl.[7] .............................................. A62B 18/08
(52) U.S. Cl. ............................ 128/206.29; 128/200.26; 128/207.14
(58) Field of Search ................... 128/200.24, 205.25, 128/206.21, 206.22, 206.24, 206.28, 206.29, 207.14, 207.15, 207.17, 202.28, 203.11, DIG. 26, 912

(56) References Cited

U.S. PATENT DOCUMENTS

| 3,056,402 A | | 10/1962 | Dickinson ................... 128/141 |
|---|---|---|---|
| 3,809,079 A | * | 5/1974 | Buttaravoli ............ 128/202.28 |
| 3,854,473 A | * | 12/1974 | Matsuo ................... 128/207.14 |
| 4,449,526 A | * | 5/1984 | Elam ...................... 128/206.21 |
| 4,470,413 A | * | 9/1984 | Warncke ................ 128/201.18 |
| 4,559,940 A | | 12/1985 | McGinnis ............... 128/206.26 |
| 4,580,556 A | * | 4/1986 | Kondur ................. 128/206.28 |
| 4,848,331 A | * | 7/1989 | Northway-Meyer ... 128/200.26 |
| 4,890,609 A | * | 1/1990 | Wilson, II ............. 128/206.29 |
| 4,971,053 A | | 11/1990 | Tarrats .................. 128/205.19 |
| 5,197,463 A | * | 3/1993 | Jeshuran ................ 128/207.14 |
| 5,339,808 A | * | 8/1994 | Don Michael ......... 128/207.15 |
| 5,558,082 A | * | 9/1996 | Spencer ................. 128/200.26 |
| 5,694,929 A | * | 12/1997 | Christopher ........... 128/207.14 |
| 5,964,217 A | * | 10/1999 | Christopher ........... 128/200.26 |
| 6,405,725 B1 | * | 6/2002 | Christopher ........... 128/200.26 |

* cited by examiner

Primary Examiner—Aaron J. Lewis
Assistant Examiner—Joseph F. Weiss, Jr.
(74) Attorney, Agent, or Firm—J. Bruce Hoofnagle

(57) ABSTRACT

A mask to facilitate ventilation of a patient. The mask has a face piece, an oropharyngeal airway, and an ambu bag. The oropharyngeal airway is incrementally movable to move the patient's tongue to clear the patient's oropharynx and to assist in sealing the face mask to the patient's face. A method of use is disclosed.

23 Claims, 4 Drawing Sheets

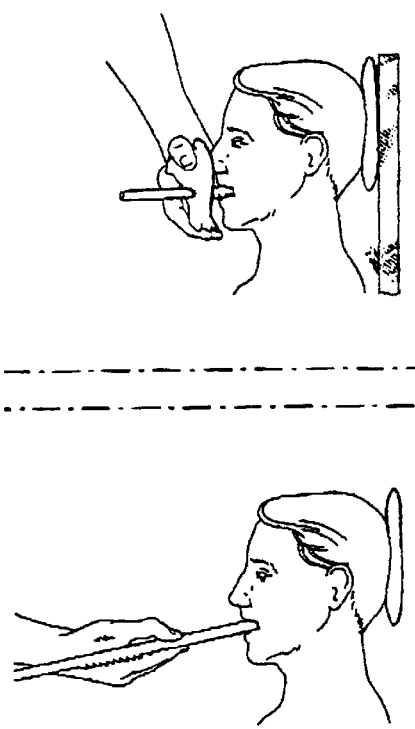

Fig 8: WHILE STILL HOLDING THE MASK AGAINST THE PATIENTS FACE WITH ONE HAND, PUMP THE AMBU BAG TO ADMINISTER OXYGEN WITH THE OTHER HAND.

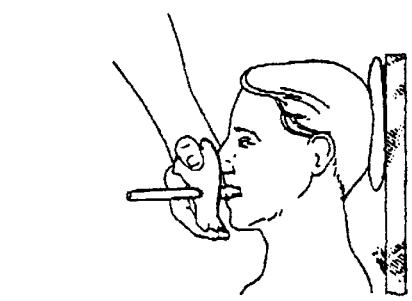

Fig 7: WHILE HOLDING MASK SNUGLY AGAINST PATIENT'S FACE WITH ONE HAND, THE OTHER HAND MOVES THE ADJUSTING MEANS TO INCREMENTALLY MOVE OROPHARYNGEAL AIRWAY OUTWARDLY FROM THE FACE PIECE TO A DESIRED POSITION.

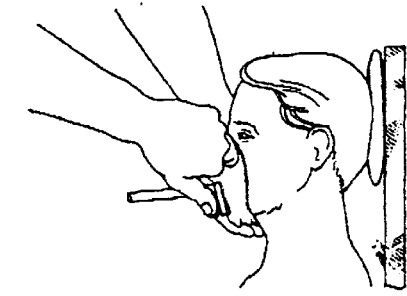

Fig 6: PLACE FACE MASK OVER PATIENT'S FACE WITH THE AIRWAY RECEIVED IN THE SLOT IN THE FACE PIECE, THE FINGERS OF THE RESCUER ARE RECEIVED IN THE FINGER GRIPS IN THE FACE PIECE.

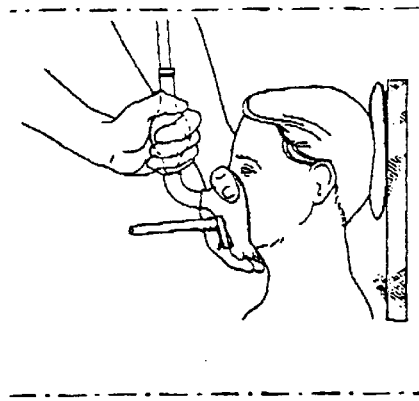

Fig 5: INSERT FIRST END OF AIRWAY INTO OROPHARYNX OF PATIENT.

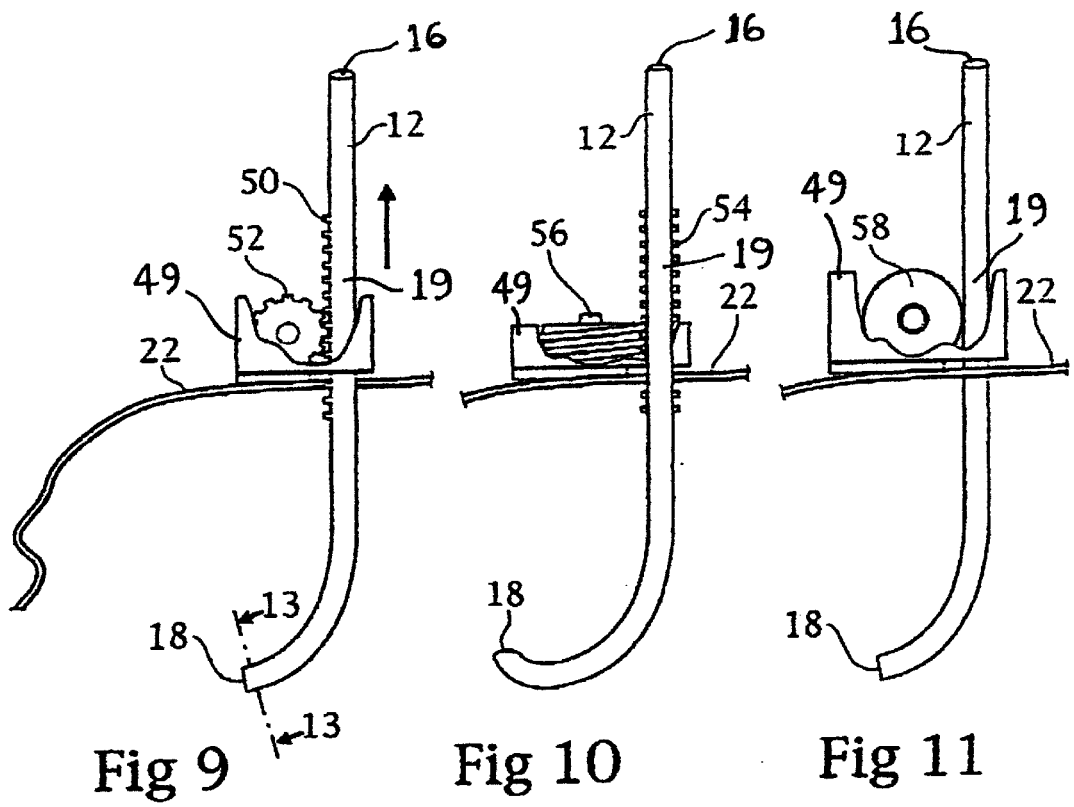
Fig 9  Fig 10  Fig 11
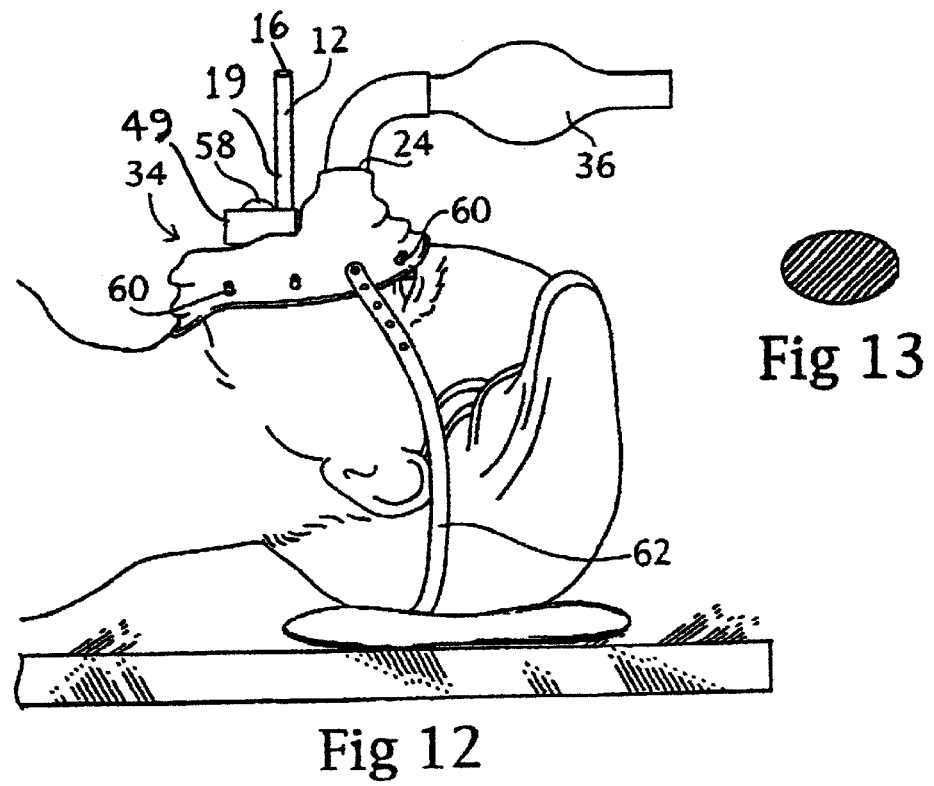
Fig 12
Fig 13

ADJUSTABLE VENTILATION MASK FOR A PATIENT

CROSS REFERENCE TO RELATED APPLICATION

The present application is related to application Ser. No. 09/921,365 entitled "DOUBLE BARREL VENTILATION MASK FOR A PATIENT" which is being filed concurrently herewith.

BACKGROUND OF THE INVENTION

The present invention relates to a face mask for ventilation of a patient and more particularly to a face mask which provides an improved seal between the face mask and the patient's face.

RELATED ART

The standard masks currently available for a rescuer or anesthetist attempt to perform the basic function of patient ventilation. A patient who has become unconscious from accidental injury, medical reasons or medications administered requires skilled or relatively untrained medical personnel to provide the basic function of breathing (i.e., ventilation). Many patients are able to be adequately ventilated with the masks currently available; however, there are a significant number of patients who cannot be adequately ventilated. This scenario will lead to anoxic brain injury and death if not quickly addressed. Patients must be ventilated and oxygenated by first responders until paramedics arrive or by hospital personnel until a physician is available to secure the airway usually by tracheal intubation. The patients at increased risk of poor mask ventilation include those who suffer from obesity, obstructive sleep apnea, congenital and acquired facial deformity, patients with beards, facial or airway edema, patients with excessive oral secretions, patients without teeth and occasionally someone who appears an "easy to mask ventilate". Endotracheal intubation can be attempted in these patients; however, this is not immediately available outside of the operating room. The patient's survival depends on the temporizing measure of mask ventilation before tracheal intubation becomes available, and even then these same people are at risk to be "difficult intubations" when compared with the general population. In addition, in many parts of the country where advanced life support is unavailable, endotracheal intubation is not even an option. The final step of providing a surgical airway through an incision in the neck is again a limited option, as most physicians are not skilled in this procedure, and most pre-hospital personnel are not trained to perform this procedure. Death and brain injury are guaranteed results from obstructed airways due to inadequate ventilation.

The problem that occurs in patients who are difficult to mask ventilate results from inadequate facial seals despite an inflated rim and inadequate delivery of oxygen past redundant oral or pharyngeal tissues which act to block oxygen flow. In an effort to correct these problems, medical personnel may insert a separate oropharyngeal or nasopharyngeal airway, but the rescuer must obtain an adequate facial seal in order for these to function effectively, and usually this remains problematic, especially since the basic airway training may be remote and experience limited.

Secondly, if an adequate facial seal is obtained, the rescuer must rely on indirect currents of air passively entering the aforementioned airways from trapping between mask and face. This low-pressured air must not only enter the oropharyngeal or nasopharyngeal airway, but then must have enough force to pass redundant soft tissue in the mouth or oropharynx to enter the trachea.

The applicant is aware of U.S. Pat. No. 3,056,402 to Dickinson which discloses a respiratory mask having a head harness, molded rubber fore piece and pipe for oxygen which is designed for aviation use.

SUMMARY OF THE INVENTION

It is an object of the present invention to provide a mask to improve the ability to ventilate marginally ventilated patients or to obtain ventilation and oxygenation in a patient with an obstructed airway.

It is a further object of the present invention to provide a face mask with an adjustable oropharyngeal probe which draws the mask more closely to the patient's face while moving the tongue anterior and improving passage of oxygen behind the tongue and into the trachea.

In accordance with the teachings of the present invention, there is disclosed a mask mountable on a face of a patient. The patient has a face, a chin, a nose, a mouth, a tongue and an oropharynyx. A face piece covers the mouth and nose of the patient. A ventilation port is formed on the face piece. A slot is formed in the face piece opposite the patient's mouth. A peripheral cuff is formed around the face piece, the peripheral cuff forming a seal with the patient's face. A oropharyngeal probe is received in the slot of the face piece. The oropharyngeal probe has a first end extending outward from the face piece and a second end locatable in the oropharynx of the patient. Means is provided for incrementally moving the oropharyngeal probe within the slot. Operating the means in a first direction moves the oropharyngeal probe outwardly disposing the cuff of the face piece snugly on the face of the patient and pulling the tongue of the patient anteriorly.

In further accordance with the teachings of the present invention, there is disclosed a mask mountable on the face of a patient. The mask has a face piece having an opening therein. An oropharyngeal probe is received in the opening in the face piece. The oropharyngeal probe has a first end extending outward from the face piece and a second end locatable in the patient's oropharynx. Means are provided for moving the oropharngeal probe with the slot wherein the face piece is fitted snugly over the face of the patient.

In another aspect, there is disclosed a method of ventilating a patient having a face, a chin, a nose, a mouth, a tongue and an oropharynx. A face mask is provided having a face piece, the face piece has a ventilation port and a slot formed therein. A peripheral cuff is formed around the face piece. An oropharyngeal probe is received in the slot in the face piece. A resuscitator bag is connected between a source of oxygen and the ventilation port. Means for moving the oropharyngeal probe are formed between the face piece and the oropharyngeal probe. The face piece is disposed over the mouth and nose of the patient. The means is operated to move the oropharyngeal probe outwardly from the face piece, pulling the patient's tongue anteriorly and disposing the cuff of the face piece snugly on the face of the patient. The resuscitator bag is pumped to administer oxygen through the face piece to the patient.

These and other objects of the present invention will become apparent from a reading of the following specification, taken in conjunction with the enclosed drawings.

BRIEF DESCRIPTION OF THE DRAWINGS

FIGS. 5–8 are a sequence of side elevation views showing use of the present invention.

FIG. 9 is a partial cutaway view showing a toothed wheel engaging teeth on the oropharyngeal probe.

FIG. 10 is a partial cutaway showing a worm gear engaging worm threads on the oropharyngeal probe.

FIG. 11 is a partial cutaway view showing a friction roller engaging the oropharyngeal probe.

FIG. 12 is a perspective view showing an adjustable length strap connected to the face piece and disposed about the patient's head.

FIG. 13 is a cross sectional view taken across lines 13—13 of FIG. 9 showing the cross section of the oropharyngeal probe.

DESCRIPTION OF THE PREFERRED EMBODIMENT

Figure 1:
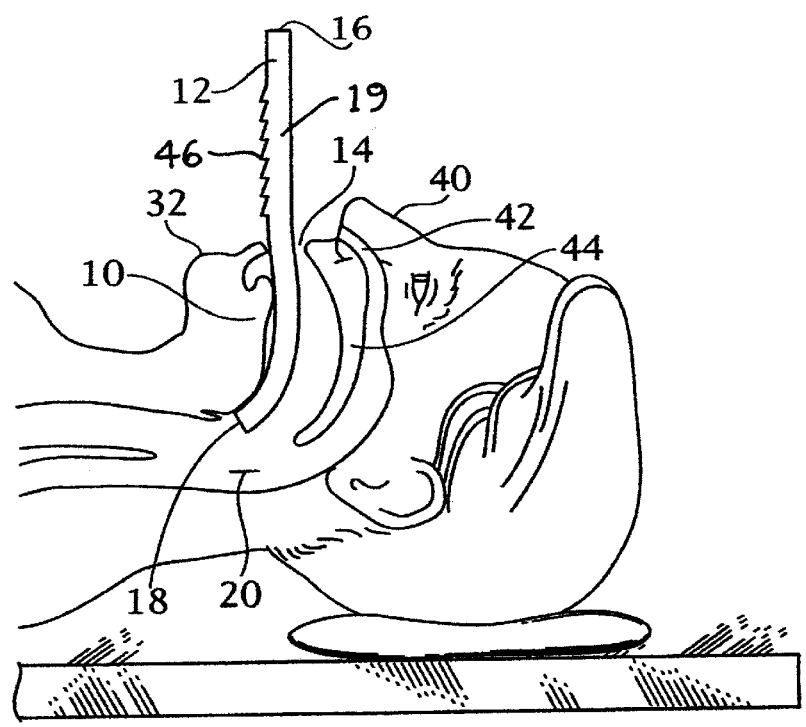
FIG. 1 is a diagrammatic view showing an oropharyngeal probe disposed in the mouth of a patient.

A patient in need of ventilation frequently is unconscious, in a supine position, and the patient's tongue 10 has fallen toward the back of the patient's neck and completely, or at least partially, blocks an air passage in the patient's oropharynx 20. As shown in FIG. 1, a portion of an oropharyngeal probe 12 is placed in the patient's mouth 14. Preferably, the oropharyngeal probe 12 is solid, as shown in FIG. 13, but could be hollow and still function in accordance with the principles of the invention. The oropharyngeal probe 12 is formed with a first end 16, a second end 18 and an intermediate portion 19 extending between the first end and the second end. With respect to the intermediate portion 19 of the oropharyngeal probe 12, the second end 18 is formed at an angle and is preferably curved. The first end 16 of the oropharyngeal probe 12 extends outwardly from the patient's mouth 14 and the second end 18 of the oropharyngeal probe is locatable in the oropharynx 20 of the patient. The angled second end 18 of the oropharyngeal probe 12 engages the back of the tongue 10 such that moving the oropharyngeal probe 12 in a direction outwardly from the mouth 14 moves the tongue 10 in the same direction to provide clearance in the air passage of the patient's oropharynx 20. This will be further described.

A face piece 22 (FIGS. 2–3) is made of an air permeable material such as rubber, plastic or treated fabric, which is preferably flexible. A ventilation port 24 is formed on the face piece 22. A slot 26 is formed in the face piece 26, and is disposed opposite from the patient's mouth 14 when the face piece 22 is placed on the patient's face as will be described. The face piece 22 has a peripheral cuff 28 formed thereon, which forms a seal with patient's face when the face piece 22 is urged onto the face of the patient. Preferably, the peripheral cuff 28 is padded or inflated, or has a design to form a leak resistant seal with the patient's face.

The face piece 22 has a chin portion 30 which fully encloses the chin 32 of the patient when the face piece 22 is placed on the patient.

Figure 4:
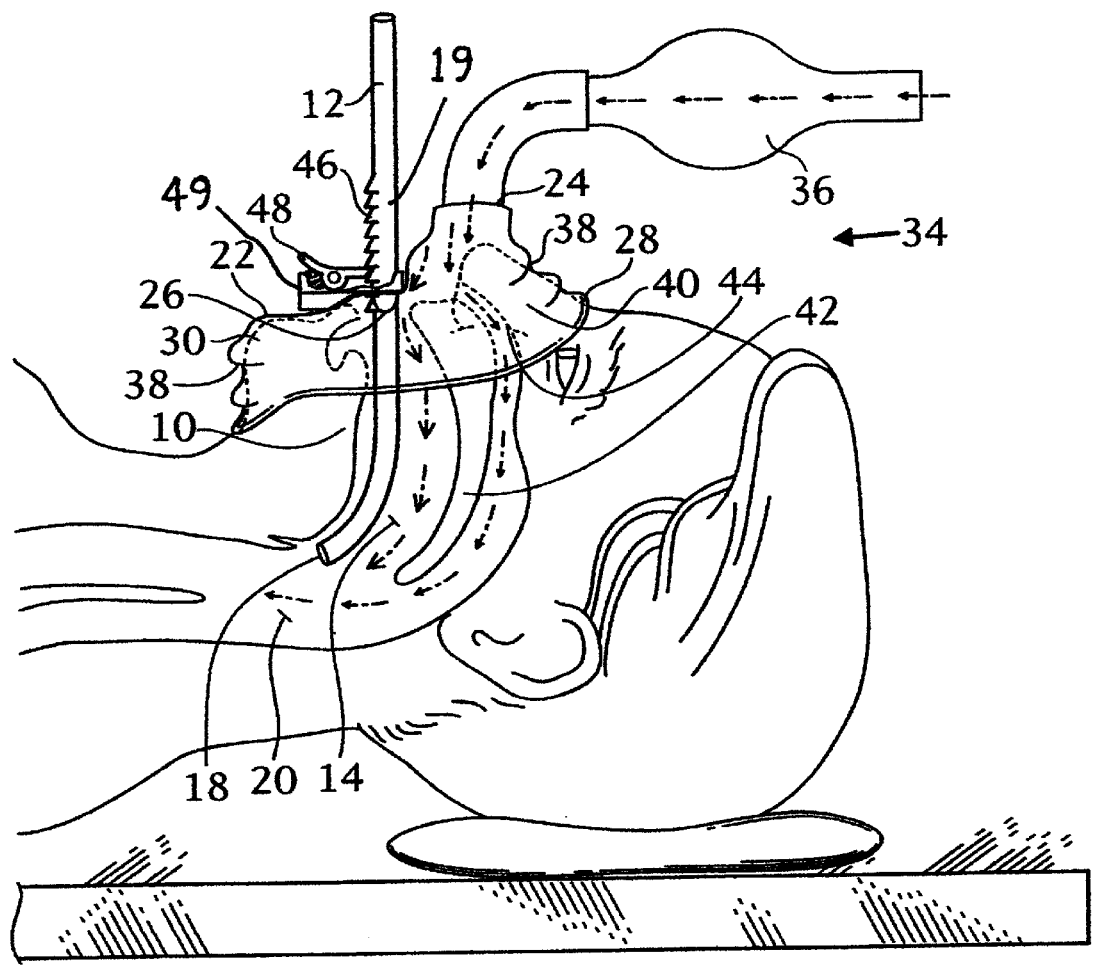
FIG. 4 is a diagrammatic view showing the face mask of the present invention disposed on the face of the patient.

Referring to FIG. 4, a face mask 34 has the face piece 22, the oropharyngeal probe 12 and a resuscitator bag 36. The oropharyngeal probe 12 is received in the slot 26 in the face piece 22 such that the first end 16 of the oropharyngeal probe 12 extends outwardly from the face piece 22. The face piece 22 is so oriented on the patient's face that the slot 26 is opposite the patient's mouth 14 with the second end of the oropharyngeal probe 12 disposed in the oropharynx 20 of the patient.

Figure 2:
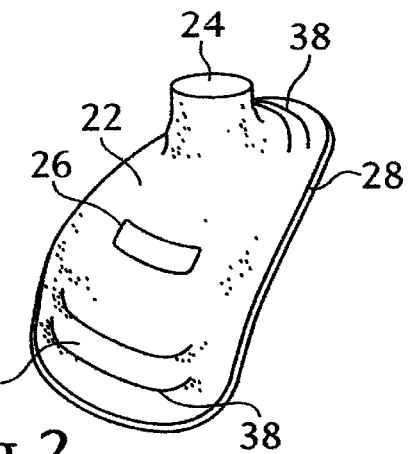
FIG. 2 is a perspective view of a face piece of the present invention.
Figure 3:
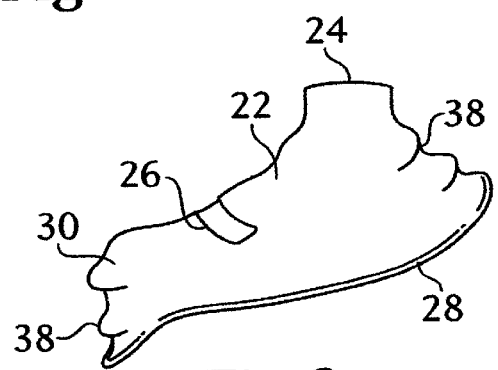
FIG. 3 is a side elevation view of the face piece of the present invention.

Preferably, the face piece 22 has at least one finger grip 38 formed thereon as shown in FIGS. 2, 3 and 4. The finger grips 38 are to receive the fingers of the person providing the ventilation to the patient. The finger grips 38, formed on the chin portion 30 of the face piece 22, enable the rescuer or health care professional (ambulance attendant, paramedic, nurse, physician, etc.) to hold the face mask 34 more firmly against the face of the patient. In the usual practice, the rescuer is positioned above the head of the patient and grasps the face mask 34 with fingers under the chin 32 and the thumb on the portion of the face mask 34 over the nose 40 of the patient. Finger grips 38 are also formed on the face piece 22 where the face piece 22 is supported by the nose 34 of the patient. In this manner, the rescuer presses on the face mask 34 improving the seal formed by the peripheral cuff 28 and simultaneously lifting the patient's head upwardly toward the rescuer and backwardly with respect to the patient to assist in clearing the air passage in the oropharynx 20 of the patient.

The resuscitation bag 36 is connected to the ventilation port 24 on the face piece 22. Oxygen is introduced into the bag 36 and pumping the bag 36 forces the oxygen into the air passage of the patient. The oxygen enters both the nasal passage 42 and the oral passage (mouth) of the patient on either side of the palate 44 of the patient as shown by the arrows in FIG. 4. A separate oropharyngeal or nasopharyngeal airway can be placed to assist with the effective ventilation and oxygenation.

The sliding movement of the oropharyngeal probe 12 in the slot 26 in the face piece 22 is controlled by a means for incrementally moving the oropharyngeal probe relative to the face piece. In one embodiment (FIG. 4) the intermediate portion 19 of the oropharyngeal probe 12 has a plurality of spaced apart saw teeth 46 formed or, in the alternative, located thereon. A pawl 48 is movably affixed, for pivoting movement, to a bearing block 49, which is mounted exteriorly on the face piece 22 such that the pawl 48 is positioned to engage the saw teeth 46 on the oropharyngeal probe 12 and the bearing block bears against the exterior of the face piece. Pivoting the pawl 48 on the bearing block 49, results in a ratcheting action between the saw teeth 46 and the pawl to move incrementally the oropharygngeal probe in a first direction outwardly through the slot 26 in the face piece 22. This movement of the probe 12 causes the curved second end 18 of the probe 12 to fully contact the base of the patient's tongue 10 adjacent the oropharynx 20 and to move the tongue 10 anteriorly toward the face mask 34 at the front of the patient's mouth 14. In this manner the oropharaynx 20 of the patient becomes unobstructed providing clear oral and nasal passages for the flow of oxygen into the patient's lungs. The ratcheting of the pawl 48 causes the bearing block 49 to further press against the face of the patient forming a better seal between the cuff 28 on the face piece 22 and the patient's face.

The means for incrementally moving the oropharyngeal probe 12 relative to the face piece 22, in a first embodiment illustrated in FIG. 4, is formed by a first portion thereof, which includes the bearing block 49 and the pawl 48 mounted for movement on the bearing block. A second portion of the means for incrementally moving the oropharyngeal probe 12 relative to the face piece 22 includes the teeth 46 located on the oropharyngeal probe.

The second end 18 of the oropharyngeal probe 12 may have a greater curvature more nearly "J" shaped as shown in FIG. 10. This configuration more positively engages the base of the patient's tongue 10 and provides greater assurance that the oral passage is unobstructed. This alternate embodiment is shown in FIG. 10 for illustration only. Any embodiment of the probe 12 may be used with any embodiment of the means for incrementally moving.

FIGS. 5–8 show the sequence of use of the present invention.

Alternately, the oropharyngeal probe 12 may be disposed in the slot 26 in the face piece 22 before placing the face piece on the face of the patient. The oropharyngeal probe 12 is then inserted into the mouth 14 and oropharynx 20 of the patient and the face piece 22 is slid down on the probe 12 and seated on the patient's face.

Alternately, in a second embodiment of the means for incrementally moving as shown in FIG. 9, a plurality of spaced apart teeth 50 are formed on the intermediate portion 19 of the oropharyngeal probe 12. A toothed wheel 52 is attached for rotation to the bearing block 49, which is mounted exteriorly on the face piece 22 such that the toothed wheel 52 engages the teeth 50 on the oropharyngeal probe 12 in a rack-and-pinion manner. Preferably the teeth 50 are square or rectangular. Rotation of the toothed wheel 52 incrementally moves the oropharyngeal probe 12 to slide within the slot 26 in the face piece 22 to move the tongue 10 of the patient and to assist in forming a seal between the cuff 28 and the face piece 22 on the patient's face. In the second embodiment, a first portion of the means for incrementally moving includes the bearing block 49 and the toothed wheel 52, while a second portion of the means includes the teeth 50 located on the oropharyngeal probe 12.

In a third embodiment of the means to effect movement of the oropharyngeal probe 12 in the slot 26 in the face piece 22 is shown in FIG. 10. The intermediate portion 19 of the oropharyngeal probe 12 has worm threads 54 formed thereon. A worm gear 56 is attached to the bearing block 49 on the face piece 22 such that the worm gear 56 engages and cooperates with the worm threads 54. Tn this manner, movement of the worm gear 56 produces movement of the oropharyngeal probe 12. In the third embodiment, a first portion of the means for incrementally moving includes the bearing block 49 and the worm gear 56, while a second portion of the means includes the worm threads 54 formed on the oropharyngeal probe 12.

A fourth embodiment of the means for providing incremental sliding movement of the oropharyngeal probe 12 within the slot 26 of the face piece 22 is shown in FIG. 11. A roller means 58 having a gripping outer surface is connected to the bearing block 49 on the face piece 22. The gripping outer surface contacts the oropharyngeal probe 12 and frictionally moves the probe 12 within the slot 26 in the face piece 22. In the fourth embodiment, a first portion of the means for incrementally moving includes the bearing block 49 and the roller 58, while a second portion of the means includes the gripping outer surface formed on the oropharyngeal probe 12.

Other means may be used to adjust the disposition of the oropharyngeal probe 12 with respect to the face piece 22 without departing from the spirit and scope of the invention.

Figure 2A:
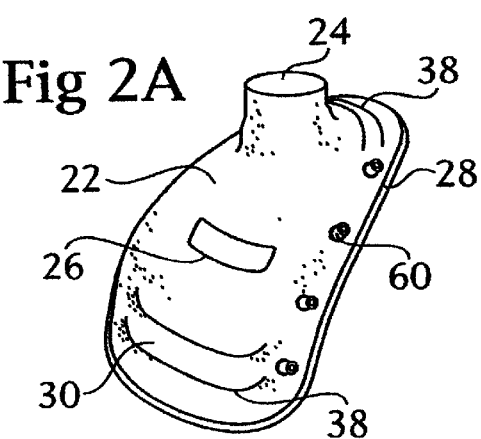
FIG. 2A is a perspective view of the face piece of the present invention with means for attaching a strap.
Figure 3A:
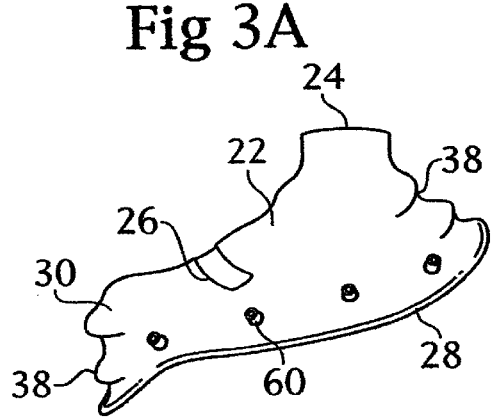
FIG. 3A is a side elevation view of the face piece of the present invention with means for attaching a strap.

To further assist in sealing the face mask 34 to the patient, a plurality of spaced apart protrusions 60 are formed on the face piece 22, extending outwardly therefrom (FIGS. 2A, 3A and 12). At least a pair of protrusions 60 are formed on opposite sides of the face piece 22. At least one strap 62 is connected between the at least one pair of protrusions 60 such that the at least one strap 62 is connected to one of the protrusions 60, extends around the head of the patient and is connected to another of the protrusions of the pair on the opposite side of the face piece 22. There may be more than one strap 62 which is disposed higher or lower on the patient's head in relation to the one strap 62. The strap 62 may be an elastic band which may stretch or may have buckle, hook and loop fasteners or other means known to persons skilled in the art to provide an adjustable length of the strap. In this manner, the strap provides for use with patients having a wide variation in head size.

The face piece 22 may also be formed in several sizes to provide a better seal for patients having larger or smaller faces. The oropharyngeal probe 12 has a cross section (FIG. 13) which is larger or smaller to correspond with the size of the face piece 22 and the patient.

The face mask 34 of the present invention provides an improved ability to ventilate and oxygenate marginally ventilated patients to obtain ventilation on patients who cannot be ventilated by face masks which are presently available. The mask 34 of the present invention has the following features:

1. New design of a chin portion 30 for the mask 34 with finger grips 38 formed by grooves at proximal and distal ends which allows improved facial seal, especially when the patient's head is extended.

2. Ratchet/roller adjusted oropharyngeal probe 12 which obtains/improves oxygenation by lifting the tongue 10 anteriorly off the posterior opropharyanx 20 and maintaining its position, allowing for passage of oxygen into the trachea.

3. Same ratchet/roller adjusted oropharyngeal probe 12 which improves ventilation by improved facial seal created by tension created between oropharyngeal probe motion with concomitant downward pressure of the mask 34.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A mask mountable on a face of a patient, the patient further having a chin, a nose, a mouth, a tongue and an oropharynx, comprising:

a face piece for covering the mouth and nose of the patient, a slot formed in the face piece, an oropharyngeal probe located for movement within and relative to the slot of the face piece, with a first end of the oropharyngeal probe extending outward from the slot of the face piece and a second end of the oropharyngeal probe being locatable in the oropharynx of the patient, and means having a first portion thereof mounted on the face piece and a second portion thereof located on the oropharyngeal probe for incrementally moving the oropharnryngeal probe relative to the face piece upon operation of the means.

2. The mask of claim 1, wherein the face piece further has a chin portion enclosing the chin of the patient.

3. The mask of claim 1, further comprising at least one finger grip formed in the mask wherein external pressure is applied to the at least one finger grip to hold the mask more firmly against the face of the patient.

4. The mask of claim 3, wherein at least one finger grip is formed on a chin portion of the face piece.

5. The mask of claim 3, wherein at least one finger grip is formed on a portion of the face piece which is mountable over the nose of the patient.

6. The mask of claim 1, further having at least a pair of spaced apart protrusions extending outwardly from the face piece, at least one strap having an adjustable length being connected between the at least one pair of protrusions, the at least one strap being disposable about the patient's head and securing the mask to the patient's head.

7. The mask of claim 6, wherein the at least one strap is formed from an elastic material.

8. The mask of claim 1, wherein the first portion of the means for moving includes a plurality of spaced apart saw teeth formed on the oropharyngeal probe and the second portion of the means for moving includes a pawl disposed on the face piece, the pawl engaging the teeth on the oropharyngeal probe.

9. The mask of claim 1, wherein the first portion of the means for moving includes teeth formed on the oropharyngeal probe, the second portion of the means for moving includes a toothed wheel attached to the face piece, the toothed wheel engaging and cooperating with the teeth on the oropharyngeal probe.

10. The mask of claim 1, wherein the first portion of the means for moving includes a roller mounted on the face piece, the roller having a gripping outer surface, the second portion of the means for moving including a contact surface, the gripping outer surface of the roller contacting the contact surface of the oropharyngeal probe such that moving the roller moves the oropharyngeal probe within the slot in the face piece.

11. The mask of claim 1, wherein the first portion of the means for moving includes worm threads formed on the oropharyngeal probe, the second portion of the means for moving includes a worm gear attached to the face piece, the worm gear engaging the worm threads on the oropharyngeal probe.

12. The mask of claim 1, wherein the first end of the oropharyngeal probe is curved and is positionable within the oropharynx of the patient to contact the tongue of the patient adjacent to the oropharynx.

13. The mask of claim 1, further comprising:
the first end of the oropharngeal probe formed with a portion which is engagable with the tongue of the patient when the means is operated.

14. The mask of claim 1, further comprising,
a peripheral cuff formed around an edge of the face piece for forming a seal with the face of the patient when the face piece is placed on the face of the patient, and
means having a first portion thereof mounted on the face piece and a second portion formed on the oropharyngeal probe for incrementally moving the face piece relative to the oropharyngeal probe subsequent to placement of the mask on the face of the patient to urge the face piece toward the face of the patient and thereby urge the peripheral cuff of the face piece into sealing engagement with the face of the patient.

15. The mask of claim 14, further comprising:
the first end of the oropharyngeal probe formed with a portion which is engagable with the tongue of the patient when the means is operated.

16. The mask of claim 1, further comprising:
a ventilation port formed in the face piece.

17. The mask of claim 16, further comprising a resuscitation bag connected to the ventilation port wherein oxygen may be administered to the patient.

18. A mask to facilitate ventilation of a patient having a face and an oropharynx, the mask comprising:
a face piece having an opening therein;
an oropharyngeal probe having a first end and a second end with an intermediate portion extending therebetween;
the intermediate portion of the oropharyngeal probe being mounted for movement within the opening in the face piece;
the first end of the oropharyngeal probe locatable in the oropharynx of the patient and the second end extending outwardly from the opening of the face piece, and
means having a first portion mounted on the face piece and a second portion located on the intermediate portion of the oropharyngeal probe for moving the oropharyngeal probe relative to the opening of the face piece to urge the face piece snugly over the face of the patient.

19. A method of ventilating a patient having a face, a chin, a nose, a mouth, a tongue and an oropharynx, comprising the steps of:
providing a face mask having a face piece, the face piece having a ventilation port and a slot formed therein, a peripheral cuff being formed on the face piece, an oropharyngeal probe being received in the slot in the face piece, the oropharyngeal probe having a first end locatable in the oropharynx of the patient and a second end located outward from the slot of the face piece,
providing a means for facilitating relative movement between the face piece and the oropharyngeal probe,
locating a first portion of the means on the face piece and a second portion of the means on the oropharyngeal probe,
disposing the first end of the oropharyngeal probe in the oropharynx of the patient,
disposing the face piece over the mouth and nose of the patient, the peripheral cuff contacting the face of the patient, and
operating the means to move the oropharyngeal probe outwardly relative to the face piece.

20. The method of claim 19, wherein the face piece has a chin portion, further comprising the step of:
disposing the chin portion over the face of the patient to enclose the chin of the patient.

21. The method of claim 19, further comprising the step of;
moving the first end of the oropharyngeal probe into engagement with the tongue of the patient prior to operation of the means to pull the tongue anteriorly upon operation of the means.

22. The method as set forth in claim 19, further comprising the step of:
moving the first portion of the means relative to the second portion thereof upon operation of the means to urge the face piece toward the face of the patient and form a seal between the face and the peripheral cuff.

23. The method of claim 22, further comprising the step of;
moving the first end of the oropharyngeal probe into engagement with the tongue of the patient prior to operation of the means so that the tongue is pulled anteriorly upon operation of the means.

* * * * *